US010420613B2

(12) United States Patent
Azevedo Da Silva et al.

(10) Patent No.: US 10,420,613 B2
(45) Date of Patent: Sep. 24, 2019

(54) ORTHOPEDIC SURGERY PLANNING SYSTEM

(71) Applicants: Sara Isabel Azevedo Da Silva, Arcozelo Bcl (PT); Joao Pedro De Araujo Ribeiro, Palmeira Brg (PT); Jaime Frederico Bastos De Campos, Maximinos Brg (PT)

(72) Inventors: Sara Isabel Azevedo Da Silva, Arcozelo Bcl (PT); Joao Pedro De Araujo Ribeiro, Palmeira Brg (PT); Jaime Frederico Bastos De Campos, Maximinos Brg (PT)

( * ) Notice: Subject to any disclaimer, the term of this patent is extended or adjusted under 35 U.S.C. 154(b) by 182 days.

(21) Appl. No.: 15/542,274

(22) PCT Filed: Jan. 7, 2016

(86) PCT No.: PCT/IB2016/050065
§ 371 (c)(1),
(2) Date: Jul. 7, 2017

(87) PCT Pub. No.: WO2016/110816
PCT Pub. Date: Jul. 14, 2016

(65) Prior Publication Data
US 2018/0028265 A1 Feb. 1, 2018

(30) Foreign Application Priority Data
Jan. 9, 2015 (PT) .......................... 108139

(51) Int. Cl.
*A61B 34/10* (2016.01)
*G16H 50/50* (2018.01)

(52) U.S. Cl.
CPC ............. *A61B 34/10* (2016.02); *G16H 50/50* (2018.01); *A61B 2034/102* (2016.02);
(Continued)

(58) Field of Classification Search
CPC ........ A61B 2034/102; A61B 2034/105; A61B 2034/108
See application file for complete search history.

(56) References Cited

U.S. PATENT DOCUMENTS

| 5,824,085 A | 10/1998 | Sahay et al. |
| 5,871,018 A | 2/1999 | Delp et al. |
| (Continued) | | |

FOREIGN PATENT DOCUMENTS

| WO | 2010122145 A1 | 10/2010 |
| WO | 2014095853 A1 | 6/2014 |

OTHER PUBLICATIONS

International Search Report dated May 18, 2016 for PCT/IB2016/050065.
Written Opinion dated May 18, 2016 for PCT/IB2016/050065.

*Primary Examiner* — David W Bates
(74) *Attorney, Agent, or Firm* — Lucas & Mercanti, LLP (57) ABSTRACT

The present application presents a solution that intends to solve the problem of providing an orthopedic surgery planning system with a stereoscopic vision of the patient's lesion. Disclosed is an orthopedic surgery planning system, where a conjunction window of a 2D and 3D environments, comprises an image's axial plan (301), an image's coronal plan (302), an image' sagittal plan (303), a 3D model of an anatomical structure (304), a library templates (305), iso-surfaces (306), measurements of lengths and angles (307), orientation cube (308), and multi plans 2D in the 3D environments (309). The applicability of this technology expands to the various areas such as orthopedics, orthodontics, implantology and veterinary. In the referred areas exists a surgery planning involving the reconstruction of bone structures, which is accompanied by the preparation of the material to implant in the patient.

6 Claims, 4 Drawing Sheets

(52) U.S. Cl.
CPC ... *A61B 2034/104* (2016.02); *A61B 2034/105* (2016.02); *A61B 2034/108* (2016.02)

(56) References Cited

U.S. PATENT DOCUMENTS

| | | |
|---|---|---|
| 2005/0054917 A1 | 3/2005 | Kitson |
| 2005/0059873 A1 | 3/2005 | Glozman et al. |
| 2008/0077158 A1 | 3/2008 | Haider et al. |
| 2008/0319448 A1 | 12/2008 | Lavallee et al. |
| 2011/0214279 A1* | 9/2011 | Park ............. G06T 7/0012 29/592 |
| 2011/0257653 A1 | 10/2011 | Hughes et al. |
| 2012/0221114 A1 | 8/2012 | Meulink et al. |
| 2012/0310399 A1 | 12/2012 | Metzger |

* cited by examiner

ORTHOPEDIC SURGERY PLANNING SYSTEM

CROSS REFERENCE TO RELATED APPLICATIONS

This Application is a 371 of PCT/IB2016/050065 filed on Jan. 7, 2016, which claims priority of Portuguese Application No. 108139 filed Jan. 9, 2015, both of which are incorporated herein by reference.

TECHNICAL FIELD

The present application relates to orthopedic surgery planning system and method.

BACKGROUND

On the introduction of radiological examinations in digital format, surgeons began to have problems during the manual preoperative planning. Thus, arises the need for these surgeons to resort to alternative methods for the preoperative surgeries planning in a virtual mode, especially using medical images from the patient.

The benefits of a computer-implemented method for surgery planning are high. There is currently a great interest in the development of digital medical imaging techniques.

Document U.S. Pat. No. 5,824,085 A discloses a method, a system and an apparatus for planning the position of a prosthesis within a bone, specifically, within a long bone such as the femur, tibia, humerus, ulna and radius, including specific procedures for the total hip and knee joint replacement, long bone osteotomy, and other similar ones.

This solution generates a bone model from a digital medical image of the bone. Then a prosthetic model is selected from a library of prosthetic templates. Subsequently, a cavity model is formed based on the design of the prosthesis and/or on the bone pattern. The cavity model may then be positioned on the bone model, interactively by the surgeon or automatically through a method based on clinical parameters, to determine a reasonable location for the implantation of the prosthesis in the bone.

This solution presents some problems, particularly in the realization of automatic positioning of the prosthesis if there are any problems with the positions taken by the patient when the medical image was made. Moreover, no more than 2D models are used, which in this case reduces the stereoscopic vision of the surgeon, and also the difficulty in understanding when there are problems in a different steering axis of what is presented. In addition to the problems presented, it may also be highlighted some drawbacks to the use of this solution, since it is only directed to long bones, specifically for two types of surgery. In order to use this technology, a particular CT scan must be taken to obtain the coordinate system for the robotic system.

The solution disclosed in US 2005/054917 A1 relates to a method implemented by a computer system for planning an orthopedic surgery. Among the many features of this solution: a) provides a digital library of representative models of orthopedic prostheses; b) shows the image of the patient, showing its relevant anatomical features for orthopedic surgery; c) calibrates the medical image of the patient; d) features on the medical image of the patient a geometrical construction defined by a plurality of interrelated geometric parameters; e) allows the surgeon to reconfigure the geometrical construction by adjusting the geometric parameters according to the anatomical features of the underlying patient medical image; f) allows the selection of at least one model from the library, according to the geometric parameters established by the surgeon.

This solution presents some problems and disadvantages, such as: not using the full potential of CT and MRI; the fact that only allows 2D sectional view in three different axes, precluding the sectional view in three different axes, disabling a stereoscopic vision; and if the X-ray is done without a marker, this medical image can no longer be used for the planning of orthopedic surgery. Thus, the solution is dependent on how the imaging study is performed.

Document US 2005/059873 A1 discloses a solution related to a method and an apparatus for the preoperative planning and simulation of orthopedic surgical procedures that use medical imaging. The preoperative planning includes the acquisition, calibration and medical image registration, as well as the reduction of the fracture or the selection of the prosthesis, the application of fixative elements and the creation of the planning report.

The described method is composed of: a) obtaining the medical image; b) segmenting the anatomical structure of the medical image, such as bone, but not limiting itself only to bone segments, and manipulating the image segments to simulate a desirable result of the orthopedic surgical procedure; c) marking segments of anatomical structures in medical images; d) the performance of different measurements and analysis, such as the difference in length, angle measurements, as well as sets of more complex measurements, such as deformity analysis, structural links in terms of distances and angles between each other; e) planning that comprises means for producing output images.

This solutions presents some problems and disadvantages, such as not using the full potential of CT scan and MRI images; the fact that it only permits the cutoff in three different viewing axes which does not allow a stereoscopic vision; the impossibility of combining the cutting in different axes does not allow a clear and accurate view of what the plan to be performed; and if this is done with an X-ray without marker, this medical image can no longer be used for the planning process of orthopedic surgery. Thus, the solution is dependent on how the imaging study was performed.

Document US 2012/221114 A1 exposes a solution that refers to a case for modular components of the neck for hip prostheses. It may include indicators based on independent variables associated with the physical characteristics of the prosthesis, including leg length, offset, and anteversion. During the surgery, the surgeon may be faced with the need to change a modular neck which was selected before surgery. Thus, the surgeon may want to change at least one of the variables, for example, the leg length, offset and/or the anteversion. This way the surgeon can select, quickly and easily, a different modular neck based on the evaluation of one of the variables, without the need to reevaluate the other variables. The method described here may comprise the preoperative planning, where a template including a coordinate system is used.

This solution presents some problems and drawbacks, such as: not using any computer system that is able to validate the process defined in the solution; does not provide the surgeon with a planning process, but with a resolution at the time of the surgery; the surgeon cannot, before the surgery, have a clear and accurate view of what awaits him at the time of the surgery. If there is the possibility of making changes within the surgery room, problems may arise due to the lack of planning, and an increase of time in which the patient is exposed to infections.

The method disclosed in document WO 2014/095853 A1 is related to the generation and manufacture of a surgical guide for steering a bone surgery, and surgical guides which can be obtained by the mentioned method. More particularly, methods are provided to generate a surgical guide to steer a surgical procedure in a first bone of a patient, comprising: a) the provision of a three-dimensional model of at least a portion of the first bone and of a second bone of the patient; b) determining or identifying a contact surface on the first bone; c) identification of a contact surface on the second bone; d) determining a range of motion between the second bone and the first bone, using at least one degree of freedom; e) generation of a surgical guide.

This solution does not allow interoperation of structurally different images. The solution is related to the implementation of methods to allow determining the surgical guides which allow the realization of safer surgeries, however, it does not become an effective planning tool.

Currently it is possible to use digital methods to make the planning of the surgeries, instead of the traditional acetates. However, existing solutions only allow surgeons to perform the preoperative planning in a 2D environment. Thus, these solutions present themselves insufficient, not allowing the surgeon to evaluate, clearly and precisely, which material to be used in surgery is more appropriate for the patient in question, since they often do not have a clear understanding of the extension of the injury.

With the use of a 2D environment, faults may arise in planning and consequently in surgery due to, for example, the inappropriate choice of prosthetic material. This can result in an increased time of surgery because the surgeon may have to wait for an alternative prosthetic material or may have to make additional incisions. In addition, improper choice of the prosthetic material will likely lead to postoperative complications. All these factors tend to increase costs, requiring extra time to assist the hospital staff and the patient, and also cause increased pain and inconvenience to the latter.

The technological solutions that are intended to assist the currently existing surgical planning, have been positively evolving. However, they still do not respond to all the needs faced by the surgeons during the surgical planning. These solutions have been insufficient because they do not allow the surgeon to sufficiently clearly assess the impact of the idealized approach.

In general, any of the above solutions has the following shortcomings:
- does not allow a stereoscopic vision of the patient's lesion;
- does not allow the handling and intersection of the various 3D models—the body structures of the patient and the digital representations of the prosthetic materials;
- does not have the conjugation between 2D and 3D environments, updated in real time;
- prevents building the model from the various body structures;
- does not allow the segmentation of specific areas of the represented anatomical structures;
- complex and less appealing processes which often leads to failures in planning and later in the surgery.

In this sense, a solution that allows the surgeon to have a precise notion of what awaits him at the time of surgery is desirable.

SUMMARY

The present application discloses a method of operating an orthopedic surgery planning system, comprising the steps:
- importing at least one medical image (101);
- the user views and selects the anatomical structure (102) in the user interface, based on the medical image;
- the user selects the density values related to the anatomical structure (103) in the user interface;
- the anatomical structure 3D model is generated by the data processing means from the values selected (104), using the extraction of a polygonal mesh of an isosurface from a three-dimensional scalar field, called voxels;
- segmentation of the anatomical structure 3D model using the user interface and free manipulation of each 3D segments;
- the user selects at least one prosthetic material 3D model from the three-dimensional prosthetic material model database;
- the user inserts at least one different anatomical structure;
- the user interacts in the user interface through the multiplanar rendering module and the three-dimensional environment with the 3D models created by the data processing means;
- the data processing means generates a report with information about the planning performed.

In one embodiment the step of importing at least one medical image (101), comprises one of the following medical images:
- a Digital Radiography (X-ray);
- a Computed Tomography (CT);
- a Magnetic Resonance Imaging (MRI); or
- a Positron Emission Tomography (PET).

In other embodiment, the step of the user interacting in the user interface with the created 3D models, comprises any of:
- repositioning;
- measurement of lengths and/or angles;
- intersecting prosthetic material 3D models and anatomical structure 3D models;
- zooming;
- panning; or
- rotating, whether in 2D environment or in the 3D environment or both at the same time.

In a further embodiment, the step of the user interacting in the user interface with the created 3D models, comprises the 3D models being updated in real time in both 2D and 3D environments.

In one embodiment, the different anatomical structure is any of: skin, muscles or blood vessels.

The present application also discloses an orthopedic surgery planning system, comprising:
- a three-dimensional prosthetic material model database, comprising digital representations of at least one prosthetic material;
- a medical imaging study of the patient;
- a data processing means;
- a memory;
- user interface;
- a multiplanar rendering module;
- a three-dimensional environment module, the system configured to implement the method described in any of the previous claims.

In one embodiment, the user interface comprises a 3D environment area (105) and a 2D environment area (106) with any of the following three 2D plans: axial, coronal and sagittal.

General Description

The present application presents a solution that intends to solve the problem of providing an orthopedic surgery planning system with a stereoscopic vision of the patient's lesion.

Disclosed is an orthopedic surgery planning system, comprising:
- a three-dimensional prosthetic material model database;
- a medical imaging study of the patient;
- a data processing means;
- a memory;
- user friendly interface;
- a multiplanar rendering module;
- a three-dimensional environment module.

The present application also discloses a method of operating said orthopedic surgery planning system, comprising generating a 3D model of at least one anatomical structure based on real medical images, simulating the implant of orthopedic materials in said model, and allowing the user to evaluate and test the most suitable material.

First, the user, for example a surgeon, starts by importing at least one medical image (101), such as for example:
- a Digital Radiography (X-ray);
- a Computed Tomography (CT);
- a Magnetic Resonance Imaging (MRI); or
- a Positron Emission Tomography (PET).

In one embodiment, the medical image is imported from a communication and storage system (PACS), a Compact-Disk (CD), a folder or a Universal Serial Bus (USB) device.

Said images provide representations of an anatomical structure, for example bones, vessels, skin and muscles. This initial step is performed in a 2D environment, where the user can notice and select the anatomical structure (102).

Then, the user must select the density values related to the anatomical structure (103). These values allow to perform a segmentation of different tissues of the patient's image.

Subsequently, the 3D model of the anatomical structure is generated from the values selected (104). This step makes use of an algorithm that allows to extract a polygonal mesh of an isosurface from a three-dimensional scalar field, called voxels.

At this stage, a series of actions on the created 3D models can be performed. The user interface comprises a 3D environment area (105) and a 2D environment area (106) with three 2D plans: axial, coronal and sagittal. These two-dimensional environments are linked, which means whenever an element is moved in an environment, this change is automatically reflected in the other environment. In addition to the linking of the two environments, the user can still position the 2D plans on the 3D model of the anatomical structure, so that he can see exactly what he needs with a greater accuracy. Thus, he has a stereoscopic and more realistic view of what awaits him at the time of the surgery.

Moreover, both repositioning and zooming the 3D models of representative images, can be done whether in the 2D environment or in the 3D environment. Note also, the possibility to manipulate each 3D model individually. In the 2D environment, the surgeon may still perform measurement of lengths and angles to help him understand the extent of a lesion as well as the best size of the prosthetic material to be used.

The three-dimensional prosthetic material model database comprises digital representations of at least one prosthetic material, for example from various manufacturers (109). Some of the information stored for each entry is the company's name, the material dimensions, the material type.

These representations can be added to the 2D and 3D environments and can also be handled individually and/or together with the anatomical structures. The repositioning of the material is updated in real time in both 2D and 3D environments.

In one embodiment, in addition to the features described above, the solution allows the user to insert different anatomical structures such as the skin, in order to understand the impact of the solution found in the surrounding structures (112). Thus, the entire planning process is facilitated, allowing the user to predict the surgery and possible complications that may arise after it.

In the end a report is generated with the information regarding the performed planning.

The technology is intended for surgical planning. The applicability of this technology expands to the various areas such as orthopedics, orthodontics, implantology and veterinary. In the referred areas exists a surgery planning involving the reconstruction of bone structures, which is accompanied by the preparation of the material to implant in the patient.

With the presented solution, and contrary to what happens with other solutions, the user can perform any surgical planning in a 3D environment, where has the ability to freely and intuitively move and position the 3D models of anatomical structures generated from the medical images and the 3D digital representation of the material to implant in the surgery, thus facilitating the evaluation and selection of the most suitable materials for it. The possibility of introducing different anatomical structures allows the user to predict the impact that the planning has on the surrounding structures.

Similarly, the solution can be integrated with systems used during the surgery within the operating room. This may allow interaction with the solution using tangible interfaces, without any need for physical contact. Thus, it is possible to interact with the planning previously made in the application, at the time of the surgery.

The surgeon may still target obstructive structures with the aid of a simple and intuitive user interface (UI)/user experience (UX) design, allowing, despite the short period of time, to make the surgical planning quickly, easily and efficiently.

The present application discloses a preoperative planning methodology assisted by computer in a 3D environment, which comprises:
- selecting a value or set of density values (103) from which is constructed the 3D model of the patient's anatomical structure from his medical image (104);
- provide a 3D model library which represents the prosthetic materials;
- selecting at least one 3D model of the material from the library of digital representations, according to the interests of the surgeon and making their inclusion in the 3D environment (109);
- individually manipulate the 3D and 2D models;
- interoperation between the 2D and 3D environments, always updated in real time;
- moving freely and rotating 3D models representative of the prosthetic materials to be used in the surgery;
- intersection of the different 3D models representing the prosthetic materials and the different anatomical structures of the patient, allowing that the surgeon can understand the intersection between the material and anatomical structure;
- manual and/or automatically segmentation of anatomical structures from the medical images of the patient, e.g. the foot's bones are split and it is possible a free manipulation of each 3D segments (107).

Previously documented techniques on the 3D reconstruction, only allowed that, to reconstruct a 3D model through methods from imaging studies. However, none allows the combination of models originated from structurally different images.

The present solution allows precisely to overcome this enormous difficulty in combining structurally different images. On the one hand, the images originated from the imaging studies are characterized by material volumetric images composed of arrays of voxels. On the other hand, the digital representations of the prosthetic material whose image is vectorial and consisted of a set of geometric representations. One can understand the difficulty of inter-operation between the two types of image.

Thus, the technology inherent in this solution is related to a method which enables the interoperation of structurally different images. The implementation of this method allows the extraction of 3D models from different density values, for example the x-ray intensity from the patient's medical image and the use of 3D models representative of the surgical material by a health professional at the time of the surgery. Note also, that this technology allows individual handling of different generated models.

The developed technology presents itself as an attractive alternative because:
- the planning is always done in a 3D environment with the help of 2D views—Axial, Coronal and Sagittal (updated in real time even with the introduction of digital representations of the prosthetic material);
- the surgeon can manipulate and intersect the different generated models, by using a stereoscopic and more realistic view of what awaits him at the time of the surgery.
- is a support tool for the surgeon to understand the impact of the solution found has in the surrounding structures, because the software also allows to insert different body structures, such as a skin layer;
- allows the segmentation of the generated 3D model in order to divert the structures that obstruct the visibility;
- presents a UI/UX design simple and intuitive, allowing the surgeon, despite the short period of time, to perform the surgical planning quickly, easily and efficiently;
- includes 3D digital representations of the prosthetic material coming from the different companies in this area.

Digital images can be stored in a central archive in the hospital and be accessed from a workstation or a computer positioned on a local computer network within the hospital or from remote machine. In addition, images can be easily and quickly transmitted between hospitals, if the patient is transferred.

These characteristics are shown advantageous over conventional methods that, often only deal with a single version of the image; are expensive to produce, are delayed if it is necessary to transfer the images because normally are sent by internal and/or external mail; and images are often prone to be lost or damaged. Moreover, it is scientifically noticeable that the digital imaging techniques have evolved positively in the recent years, the images themselves use a higher quality.

The solution refers to a method which enables interoperation of structurally different images.

The application of this method allows the extraction of 3D models from different X-ray intensity values and the use of 3D images representative of the material to be used at the time of the surgery.

The described methodology allows a 3D planning environment, thereby providing the surgeon with greater accuracy, thus avoiding the selection of an unsuitable prosthesis and therefore leading to the success of the surgery.

The solution was developed with a high proximity to the medical community. A simple and intuitive application was created, reducing the learning curve and the surgical planning time.

The technology related to the solution presents itself as a more advantageous computer system because it allows:
- Greater accuracy in planning—besides the 3D environment visualization, the solution allows the conjugation in real-time of both 2D and 3D environments;
- Greater autonomy—the surgeon has complete movement freedom, to manipulate, intersect and position the different models generated in both 2D and 3D environments, allowing a stereoscopic and more realistic view of what awaits him at the time of surgery;
- Understanding of surgical complications—the generation of different anatomical structures helps the surgeon to understand the impact of the defined approach found in the surrounding structures;
- Increased visibility—the possibility of segmenting the generated 3D model allows a clear view of anatomical areas of difficult access by normal medical images;
- Intuitive and appealing—the fact that it is an easily used tool, allows the surgeon to invest the minimum time as possible in the planning of their surgeries.

The ability of the surgeon to predict the surgery influences the incidence of failure, and consequently improves the reputation of the surgeon. Also for noting, the possibility of reducing the time of the surgery and the increase of surgical productivity. The surgeon may also previse the material that will be used in surgery, in order to improve the alignment and the appropriateness of the surgical team, as well as the reduction of waste disposal costs.

All the planning of the surgery may also be presented to the patient, so that he understands more clearly the steps to be performed. This monitoring can reassure the patient and increase his security on the surgeon and all the planning.

BRIEF DESCRIPTION OF DRAWINGS

Without intent to limit the disclosure herein, this application presents attached drawings of illustrated embodiments for an easier understanding.

FIG. 1 illustrates an embodiment of the planning workflow for an orthopedic surgery, where the reference numbers show:
- 101—import patient's medical image;
- 102—2D viewer;
- 103—select the density value of the anatomical structure;
- 104—generate anatomical structure 3D model;
- 105—3D environment;
- 106—2D environment (axial, coronal and sagittal plans);
- 107—segmentation, zoom and move of the anatomical structure 3D model in the 3D environment;
- 108—zoom of the anatomical structure 3D model in the 2D environment;
- 109—select the 3D model of the prosthetic material from the library of digital representations;
- 110—zoom, pan and move of the 3D model of the material in the 3D environment;
- 111—zoom and pan of the 3D model of the material in the 2D environment;
- 112—add several 3D layers of patient's anatomical structures;
- 113—zoom and move the 3D layers of patient's anatomical structures; and
- 114—final report of the 3D planning.

MODE(S) FOR CARRYING OUT EMBODIMENTS

Referring to the drawings, herein are described optional embodiments in more detail, which however are not intended to limit the scope of the present application.

Figure 1:
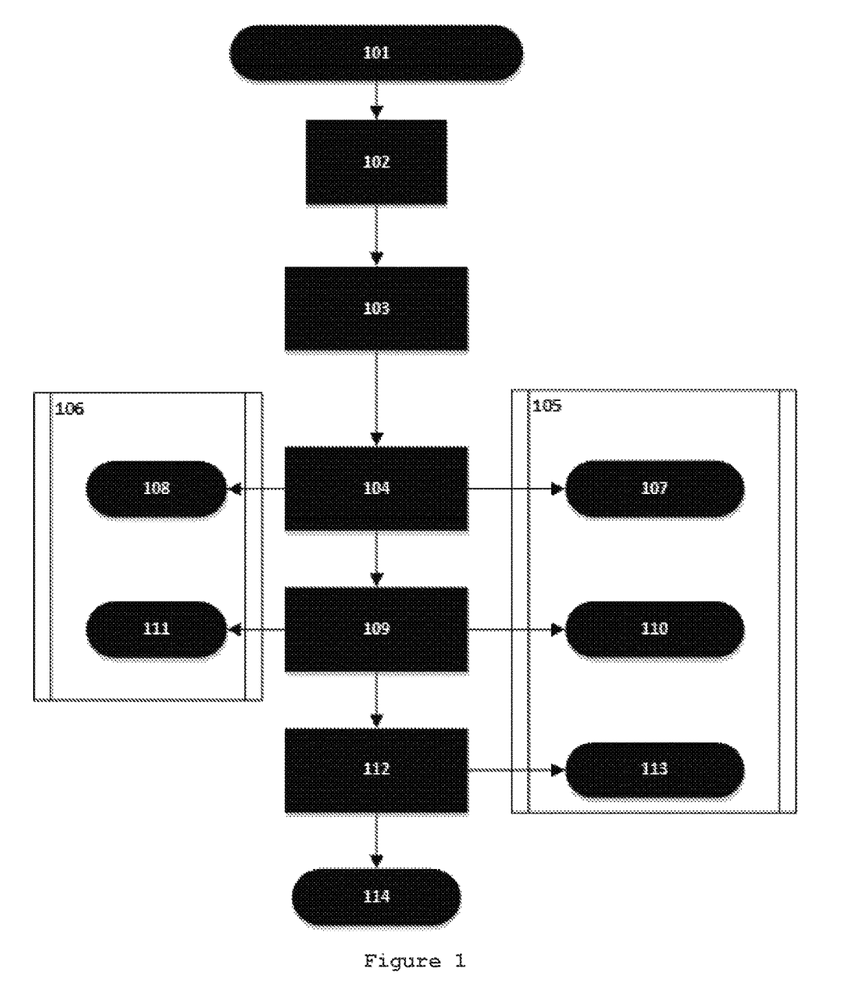

This solution allows its usage for planning in the orthopedic area, especially in the reconstruction of bone tissue and consequent surgical planning according to the illustrated embodiment of the planning workflow for an orthopedic surgery, in FIG. 1.

Figure 2:
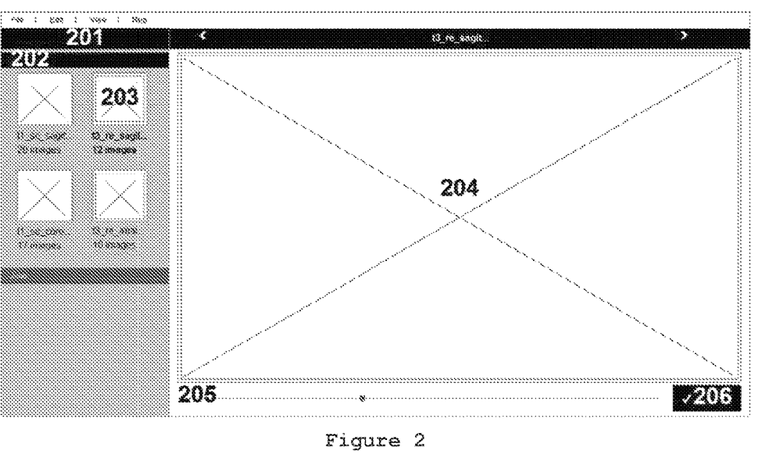
FIG. 2 illustrates an embodiment of a 2D preview window of the patient's imaging study, where the reference numbers show:
- 201—patient's list;
- 202—patient name;
- 203—patient imaging series;
- 204—2D patient image;
- 205—select the slice of the patient's image; and
- 206—create a 3D model of the anatomical structure of the patient.
Figure 3:
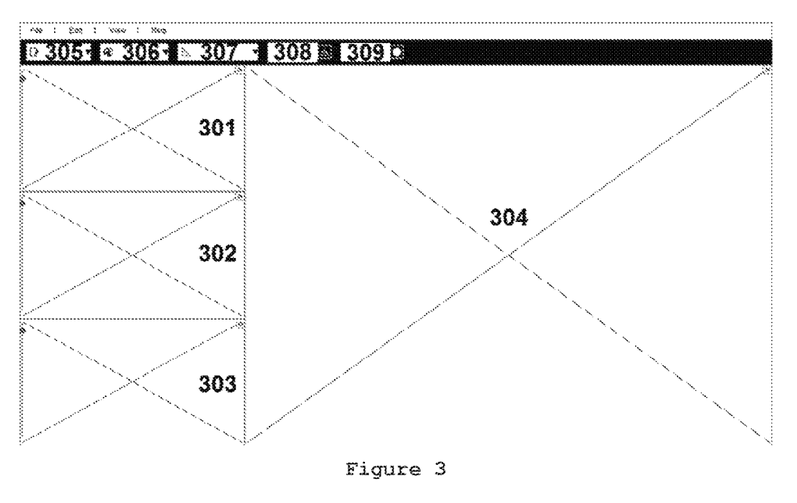
FIG. 3 illustrates an embodiment of a conjunction window of the 2D and 3D environments, where the reference numbers show:
- 301—image's axial plan;
- 302—image's coronal plan;
- 303—image's sagittal plan;
- 304—3D model of an anatomical structure;
- 305—library templates;
- 306—isosurfaces;
- 307—measurements of distances and angles;
- 308—orientation cube; and
- 309—multi plans 2D in the 3D environments.
Figure 4:
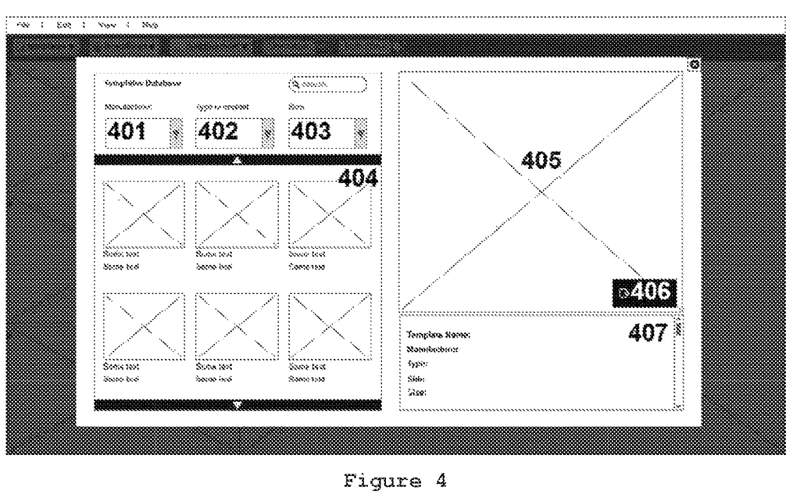
FIG. 4 illustrates an embodiment of a 3D prosthetic materials database window, where the reference numbers show:
- 401—name of the company that produces the selected prosthetic material;
- 402—template type, such as screws and plates;
- 403—dimension of the selected prosthetic material
- 404—prosthetic material list;
- 405—3D image of the prosthetic material selected;
- 406—button to add the prosthetic material to the 3D environment; and
- 407—details of the selected prosthetic material.

The presented method of operation of an orthopedic surgery planning system comprises the steps illustrated in FIG. 1:
- Import medical image;
- Present the imported medical imaging, this presentation takes place on a 2D environment (FIG. 2);
- Select a value or set of density values from which is generated the 3D model of the patient's anatomical structure from a medical image;
- Create the 3D model of an anatomical structure (FIG. 3);
- Segmentation of anatomical structures, creating 3D models that can be repositioned;
- Select 3D models representative of the prosthetic materials to use in the surgery from the three-dimensional prosthetic material model database that has these digital representations (FIG. 4);
- Generate multiple patient's anatomical structures in the 3D environment.

In one embodiment, the surgeon imports to the solution a patient's CT scan (101), being able to display in a 2D environment which bone structure he wants to rebuild (102).

In step (103), the surgeon must select the density(s) value(s) of the bone structure that he wants to rebuild. This structure is then displayed as a 3D model (104) that can be freely manipulated. To facilitate 3D visualization, the surgeon has the ability to segment the 3D model. Thus, it is possible to divert the bones that may be obstructing the visibility of a patient's injury (107).

In this multiplanar environment the surgeon can add, from a database, the prosthetic material (109) which will be used during the surgery (from various manufacturers). These materials are added to both 2D and 3D environments and can be repositioned as the surgeon deems most relevant. Thus, the surgeon has a tool that allows him to predict in a 3D way which approach is best to be used in the surgery. In addition, the surgeon can insert, in the 3D environment, 3D surrounding anatomical structures (112) that can help in the planning process.

On the window in which the 3D model appears, the surgeon can also find the CT's cuts in three axes (Axial, Coronal and Sagittal). Both 2D (105) and 3D (106) environments are updated in real time.

All digital planning process provided by this solution also includes a number of tools that assist the surgeon, such as measuring distances and measuring angles.

The present application further discloses a preoperative planning methodology assisted by computer in a 3D environment, which includes:
- the ability to take measurements of distances and angles in the 2D environment;
- multiplanar rendering of the 2D and 3D environments with the help of 2D viewing cuts—axial, coronal and sagittal;
- 3D model generation of the different anatomical structures from the patient's imaging study;
- the possibility to save the plan made for later review;
- a user-friendly design—intuitive, simple and aesthetically pleasing.

Naturally, the present embodiments are not in any way limited to the embodiments described in this document and a person with average knowledge in the field will be able to predict many possible changes to it without deviating from the main idea, as described in the claims.

The invention claimed is:

1. A method of operating an orthopedic surgery planning system, the method comprising:
   importing at least one medical image into a memory of a computer system;
   generating an anatomical structure 3D model of at least one anatomical structure, based on the at least one medical image and on a parameter that comprises one of a value or a set of density values of the at least one anatomical structure, using an extraction of a polygonal mesh of an isosurface from a three-dimensional scalar field comprising a plurality of voxels, said 3D model being a matricial volumetric image comprising a plurality of arrays of voxels;
   segmenting the anatomical structure 3D model based on the parameter;
   accessing a 3D prosthetic material model database to select at least one prosthetic material 3D model, said prosthetic material 3D model being a vectorial image comprising a set of geometric representations;
   combining a plurality of models derived from a plurality of structurally different images, by intersecting the anatomical structure 3D model and the 3D prosthetic material model;

allowing a user to interact via a user interface with the anatomical structure 3D model and the 3D prosthetic material model, in a 2D environment area and in a 3D environment area, the anatomical structure 3D model and the 3D prosthetic material model being updated in real time in the 2D and 3D environments areas, wherein the 2D environment area comprises an axial 2D plan, a coronal 2D plan, and a sagittal 2D plan;

identifying a suitable prosthetic material by performing the following steps one or more times:

inserting into the anatomical structure 3D model at least one second anatomical structure different from the at least one anatomical structure, by segmenting said anatomical structure 3D model based on the parameter;

simulating an implantation of a prosthetic material into the anatomical structure 3D model; and evaluating a suitability of the prosthetic material based on a predicted impact that a current planning might have on one or more surrounding structures and one or more predicted complications resulting from a surgery;

generating, by a processor, a report comprising information relating to the planning performed and the steps performed to identify a suitable prosthetic material; and saving the information in the memory.

2. The method according to claim 1, wherein the step of importing at least one medical image comprises importing an image generated by one of Digital Radiography (X-ray), Computed Tomography (CT), Magnetic Resonance Imaging (MRI), and Positron Emission Tomography (PET).

3. The method according to claim 1, wherein allowing the user to interact via a user interface comprises one of repositioning, measuring lengths and/or angles, intersecting the 3D prosthetic material models and the anatomical structure 3D model, zooming, panning, and rotating, in at least one of the 2D environment area and the 3D environment area.

4. The method according to claim 1, wherein the at least one second anatomical structure comprises one of bone, skin, muscles and blood vessels.

5. An orthopedic surgery planning system configured to implement the method of claim 1, the orthopedic surgery planning system comprising:

a three-dimensional prosthetic material model database, comprising digital representations of at least one prosthetic material; and a computer system comprising:

a data processor configured to create a 3D model from at least one medical image;

a three-dimensional environment module configured to generate a 3D environment;

a multiplanar rendering module configured to render a 2D environment and a 3D environment;

a user interface; and a memory.

6. The orthopedic surgery planning system according to claim 5, wherein the user interface comprises a 3D environment area and a 2D environment area.

* * * * *